(12) United States Patent
Boloor et al.

(10) Patent No.: US 9,690,861 B2
(45) Date of Patent: Jun. 27, 2017

(54) DEEP SEMANTIC SEARCH OF ELECTRONIC MEDICAL RECORDS

(71) Applicant: International Business Machines Corporation, Armonk, NY (US)

(72) Inventors: Keerthana Boloor, Elmsford, NY (US); Eric W. Brown, New Fairfield, CT (US); Murthy V. Devarakonda, Peekskill, NY (US); David Ferrucci, Yorktown Heights, NY (US); John M. Prager, Pomona, NY (US)

(73) Assignee: International Business Machines Corporation, Armonk, NY (US)

( * ) Notice: Subject to any disclaimer, the term of this patent is extended or adjusted under 35 U.S.C. 154(b) by 250 days.

(21) Appl. No.: 14/334,033

(22) Filed: Jul. 17, 2014

(65) Prior Publication Data

US 2016/0019299 A1 Jan. 21, 2016

(51) Int. Cl.
*G06F 17/30* (2006.01)
*G06F 19/00* (2011.01)

(52) U.S. Cl.
CPC .. *G06F 17/30867* (2013.01); *G06F 17/30731* (2013.01); *G06F 19/322* (2013.01)

(58) Field of Classification Search
None
See application file for complete search history.

(56) References Cited

U.S. PATENT DOCUMENTS

| 6,684,188 | B1 | 1/2004 | Mitchell et al. | |
|---|---|---|---|---|
| 8,447,783 | B2 | 5/2013 | Goping | |
| 2012/0035959 | A1* | 2/2012 | Berdia | G06F 19/325 |
| | | | | 705/3 |
| 2012/0301864 | A1 | 11/2012 | Bagchi et al. | |
| 2013/0041685 | A1 | 2/2013 | Yegnanarayanan | |
| 2013/0124523 | A1 | 5/2013 | Rogers et al. | |
| 2013/0132392 | A1 | 5/2013 | Kenedy et al. | |
| 2014/0046697 | A1* | 2/2014 | Rogers | G06F 19/327 |
| | | | | 705/3 |
| 2014/0317080 | A1* | 10/2014 | Piraino | G06F 19/322 |
| | | | | 707/706 |

OTHER PUBLICATIONS

Comprehensive description of text search in Wikipedia (http://en.wikipedia.org/wiki/Full_text_search).
Zhou et al., "SPARK: Adapting Keyword Query to Semantic Search," ISWC'07/ASWC'07 Proceeding of the 6th international the semantic web and 2nd Asian conference on Asian semantic web conference., pp. 1-14.

(Continued)

*Primary Examiner* — Jay Morrison
(74) *Attorney, Agent, or Firm* — Gibb & Riley, LLC

(57) ABSTRACT

Methods, systems, and devices provide semantically relevant information by analyzing an Electronic Medical Record (EMR) having structured data and unstructured data. In the analysis, a first set of medical concepts is identified from the unstructured data in the EMR, and a second set of medical concepts is identified from the structured data in the EMR. Relationships between medical concepts in the first set of medical concepts and the second set of medical concepts are automatically identified in a medical ontology by such methods, systems, and devices.

20 Claims, 11 Drawing Sheets

(56) References Cited

OTHER PUBLICATIONS

Garla, V. et al., "The Yale cTAKES extensions for document classification: architecture and application" Journal of the American Medical Informatics Association (2011), pp. 1-8.
David Ferrucci et al, "Watson: Beyond Jeopardy!", IBM Research Report No. RC25270, Jun. 2, 2011, pp. 1-11.
Andrew Tawfik et al., "Using Semantic Search to Reduce Cognitive Load in an Electronic Health Record", 2011 IEEE 13th Int'l Conf on e-Health Networking, Applications and Services, pp. 181-185.
Sheth et al., "Active semantic electronic medical record." The Semantic Web—ISWC 2006. Springer Berlin Heidelberg, 2006, pp. 913-926.
Al-Safadi, "Semantic-Based Exchanger of Electronic Medical Records," Proceedings of MoMM2008, pp. 418-421.
Shah et al., "Comparison of concept recognizers for building the Open Biomedical Annotator," Proceedings of the 2009 AMIA Summit on Translational Bioinformatics, pp. 1-9.
Hinds et al., "Wham!: a forms constructor for medical record access via the World Wide Web.", Proceedings of the Annual Symposium on Computer Application in Medical Care. American Medical Informatics Association, 1995, Pp. 116-120.
Bevan Koopman, "Towards semantic search and inference in electronic medical records: An approach using concept-based information retrieval", Australasian Medical Journal AM 2012, 5, 9, pp. 482-488.
Harsha Gurulingappa et al., "A Semantic Platform for Information Retrieval from E-Health Records", Jul. 15, 2014, pp. 1-9.

* cited by examiner

Annotation Results for emr_314021_5018_a_note_00067.xml in/data8/emra-work/emra-source/emr_314021_5018_a_xmicas

Click In Text to See Annotation Detail

Annotations
- SignOrSymptom
  - SignOrSymptom ('depression')
    - begin = 1133
    - end = 1143
    - links = null
    - componentId = MedicalConceptAnnotator
    - mentionType = null
    - semanticType = sosy
    - conceptName = depression
    - cui = C1579931
    - preferredName = Depressed - symptom
    - negotiation = null
    - mappings = null
    - generic = false
    - variants = {depressed - symptom, depressed, depressed
    - isInsideCui = true
    - innerConcepts = null
    - skipsTerms = false
    - confidence = 0.025

— 428

CHIEF COMPLAINT: Falls at home.

HISTORY OF PRESENT ILLNESS: The patient is an 82-year-old female who fell at home and presented to the emergency room with increased anxiety. The patient denied any chest pain or pressure and no change to exercise tolerance. The patient denied any loss of consciousness or incontinence. She denies any seizure activity. She states that she "tripped" at home. Family states she frequently takes Darvocet for her anxiety and that makes her feel better, but they are afraid she is self medicating. They stated that she has numerous medications at home, but they were not sure if she was taking them. The patient has been getting along for a number of years and has been doing well, but recently has been noting some decline primarily with regards to the depression. The patient denied SI or HI.

— 422

Legend

| | | | | | |
|---|---|---|---|---|---|
| ☐ Range | ☐ ResearchActivity | ☐ RootPredicate | ☐ SameAs | ☑ SignOrSymptom | |
| ☐ SmallWholeNumber | ☐ Source Document... | ☐ SpatialConcept | ☐ SWPattern | ☐ Symptom | |
| ☐ TemporalConcept | ☐ Term | ☐ TherapeuticOrPre... | ☐ Time | ☐ TvShow | |
| ☐ UmlsDictTerm | ☐ Unit | ☐ UnitOfMeasurement | ☐ Weight | ☐ WholeNumber | |
| ☐ XsgParse | ☐ XsgSentence | ☐ XsgTaken | ☐ XsgTopParse | ☐ Year | |

Select All | Deselect All | Hide Unselected | Sofa: EMR_View ▼

(HTN)  [Search] [Back]

| Semantic Matches | Contradicted | More General | Tests |

| Note Date | Title | Match Summary |
|---|---|---|
| Jan 17, 2011 | D/C Summary | [Hypertension] |
| Jun 23, 2011 | Progress Notes | [HTN] |
| Nov 07, 2013 | Progress Notes | [Hypertension] |
| Dec 12, 2013 | Nurse Notes | [High Blood Pressure] |

Progress Note
Date: Nov 07, 2013

240.2 Diabetes Mellitus Type 2
H-A1c7.1

401.9 Unspecified essential hypertension
BP: 120/87

272.4 Hyperlipidemia
Last Lipid Panel
CHOL 213
LDL 116
HDL 35

SUBJECTIVE: Pt with ongoing issues around his diabetic control. Have been fairly aggressively, upwardly adjusting his metformin. Pt continues to have somewhat high blood A1c. Hypertension is well controlled with medication. I talked to pt today. He feels a little fatigued. Otherwise, he is doing well. — 488

PHYSICAL EXAMINATION: Vitals as in the chart. The patient is pleasant and cooperative. He is in no apparent distress.

ASSESSMENT AND PLAN: Diabetes, still with some problematic blood A1c. Start on Actos 5mg. Follow up on A1c next month.

FIG. 5B

| Semantic Matches | Tests | Medications | Medications Ordered | |
|---|---|---|---|---|
| Order Date | Title | Match Summary | | |
| Feb 20, 2011 | Medication Ordered | [Synthroid] | 58517-080-30 Cyclobenzaprine 10 mg tablet | |
| | | | 00074-6594 Synthroid | |
| May 15, 2011 | Medication Ordered | [Levothyroxine 50 mcg] | 54458-896-02 Citalopram 20 mg tablet | |
| Oct 08, 2011 | Medication Ordered | [Levothyroxine] | 53978-3021 Levothyroxine 50 mcg tablets | |
| | | | 35356-949-30 Losartan 25 mg tablet | |
| Jan 12, 2011 | Medication Ordered | [Synthroid tablet] | 53978-3021 Levothyroxine tablets | |
| | | | 35356-949-30 Losartan 25 mg tablet | |
| | | | 00074-6594 Synthroid tablet | |

FIG. 5C

DEEP SEMANTIC SEARCH OF ELECTRONIC MEDICAL RECORDS

BACKGROUND

The present disclosure relates to electronic medical records, and more specifically, to systems and methods for deep semantic searching of electronic medical records.

An Electronic Medical Record (EMR), or Electronic Health Record, is a digital record of a patient's medical history. An EMR tracks a patient's medical history over time and may include a range of data including both unstructured and structure data. Examples of unstructured data include notes by a variety of medical care providers, for example clinician notes. Examples of structured data include procedures performed, lab results, and medications taken. Over time the amount of information in a patient's EMR can becomes very large and may make it difficult for medical practitioners to quickly and easily locate relevant information. Accordingly, there is a need for an improved system for searching for relevant information in an EMR.

SUMMARY

Disclosed herein is a system and method to search and retrieve relevant content from an Electronic Medical Record (EMR). Systems and methods herein may search both unstructured and structured components of an EMR based on a query. The query may take any form including search terms or a natural language question. The processes disclosed herein first annotate the contents of the EMR using natural language processing and semantic information extraction techniques and develop clinically relevant semantic relations among elements of the EMR (e.g. relationships between terms in a Clinical Note, and between a medication ordered/filled and a disease diagnosed). Upon receiving search terms or a question on an EMR, the processes also annotate the query, using the natural language processing and semantic information extraction techniques, then determine semantic matches in the annotated and inter-related EMR contents for the annotated input. The resulting matches are scored based on their relevance to the input and strength of relationship among relevant entries. Retrieved results with an aggregate score above a threshold are returned as a response to the query.

According to systems and methods herein, information is retrieved from a specified EMR. The retrieved information is semantically related to the search or input question. The results may include clinical relationships such as between terms in a clinical note or between medications and a disease. Example relationships include "caused by", "treats", and other medical relationships.

Therefore, according to methods herein, a search query containing search terms for information from an EMR is received. The EMR comprises structured data and unstructured data. Semantically relevant information related to the search terms is provided in response to the search query. The relevant information can comprise clinical notes, passages from clinical notes, medical concepts from passages, medications, test results, treatments, and/or contraindications in any of the above.

In other words, the contents of an EMR for a patient are analyzed. The EMR comprises structured and unstructured entries. Semantic features are extracted from the EMR by identifying medical concepts from the structured and unstructured entries. Clinically relevant semantic relationships are identified among the structured and unstructured entries within the EMR based on the medical concepts. Responsive to any form of query, such as a question, request, search term, natural language query, etc., into the EMR, annotated query contents are produced based on medical semantic concepts in the query. Results to the query are retrieved from the EMR. The results may comprise clinical notes, passages from clinical notes, medical concepts from passages, medications, test results, treatments, and/or contraindications in any of the above, from the structured and unstructured entries in the EMR. A first score for the results is produced based on degree of semantic match of the passages to the query. The results having the first score above a predetermined threshold are provided in response to the query.

According to methods herein, an EMR comprising structured data and unstructured data is analyzed. In the analysis a first set of medical concepts is automatically identified from the unstructured data in the EMR. A second set of medical concepts is automatically identified from the structured data in the EMR. Relationships between medical concepts in the first set of medical concepts and the second set of medical concepts are automatically identified in a medical ontology. The relationship information is stored as a data structure in a computerized device.

According to a computer-implemented method of providing semantically relevant information from an EMR, the contents of the EMR are analyzed and semantic features of the EMR are recognized. The contents of entries in the EMR are annotated by identifying medical concepts from the semantic features within the EMR and the syntactic features of the entries. The entries comprise structured and unstructured data. Relationships among the entries within the EMR are identified based on the medical concepts. Search indexes may be created on the EMR for queries based on the semantic features and the syntactic features. A query is received. The query is analyzed to recognize semantic features and syntactic features of the query. The contents of the query are annotated by identifying medical semantic concepts within the query based on the semantic features of the query. Annotated query contents are produced. Results to the query are obtained from the EMR, based on the annotated query contents and the search indexes, if created. The results comprise content from the EMR semantically and textually matching the query and entries having a relationship based on the medical concepts. A first score for the results is determined based on the degree of textual match of the content to the query. The content data items, for example, clinical notes, passages, terms, and structured data having the first score above a predetermined threshold are provided in response to the query.

According to systems herein, an evidence analysis module is connected to a processor. A user interface or an additional passage analysis engine is connected to the processor and a corpus of data is connected to the evidence analysis module. The user interface provides an ability to query an EMR. The processor analyzes the contents of the EMR to recognize semantic features of the EMR and annotates the entries in the EMR to identify medical concepts from the semantic features. The processor analyzes the contents of the question to recognize semantic features of the question and annotates the contents of the question to identify medical semantic concepts, producing annotated query contents. The processor searches the EMR using the annotated query contents and creates a collection of results to the query from the EMR. Each result comprises one or more passages from the EMR. The evidence analysis module provides at least a first score for the results based on the degree of semantic match of the passages to the question. The evidence analysis module may also provide a second score for the results based on the medical relationship strength to the question using information in the corpus of data. The evidence module may produce additional similar scores. The processor may optionally combine the scores into an aggregate score using a weighted average of the scores based on a statistical model. The processor provides the results having an aggregate score or raw score above a predetermined threshold(s) in response to the question.

According to a computer program product for creating a semantically searchable electronic medical record, the computer program product comprises a computer readable storage medium having program instructions embodied therewith. The program instructions are readable/executable by a processor to cause the processor to perform a method. The method comprises receiving a search query containing search terms for information from an electronic medical record (EMR). The EMR comprises structured data and unstructured data. Semantically relevant information related to the search terms is provided in response to the search query. The relevant information comprises at least one of clinical notes, medications, test results, treatments, and contraindications.

The methods may also analyze, by a processor, the contents of the EMR and recognize, by the processor, semantic features of the EMR. The contents of entries in the EMR are annotated, by the processor, identifying medical concepts from the semantic features within the EMR and syntactic features of the entries. The processor identifies relationships among entries within the EMR based on the medical concepts. The processor may create search indexes on the EMR for search terms or natural language queries based on the semantic features and the syntactic features. When the processor receives a query, the processor analyzes the query, recognizing semantic features and syntactic features of the query. The processor annotates contents of the query, identifying medical semantic concepts within the query based on the semantic features of the query. The processor produces annotated query contents. The processor obtains, from the EMR, results to the query based on the annotated query contents and the search indexes. The results comprise passages from the EMR semantically and textually matching the query and entries having a relationship based on the medical concepts. The processor determines a first score for the results based on degree of textual match of the passages to the query. The processor provides ones of the results having the first score above a predetermined threshold, in response to the query.

BRIEF DESCRIPTION OF THE DRAWINGS

The systems and methods herein will be better understood from the following detailed description with reference to the drawings, which are not necessarily drawn to scale, and in which:

FIG. 4 is an example of an annotated EMR according to systems and methods herein;

FIGS. 5A, 5B, and 5C show examples of output displays for queries according to systems and methods herein;

DETAILED DESCRIPTION

Figure 1:
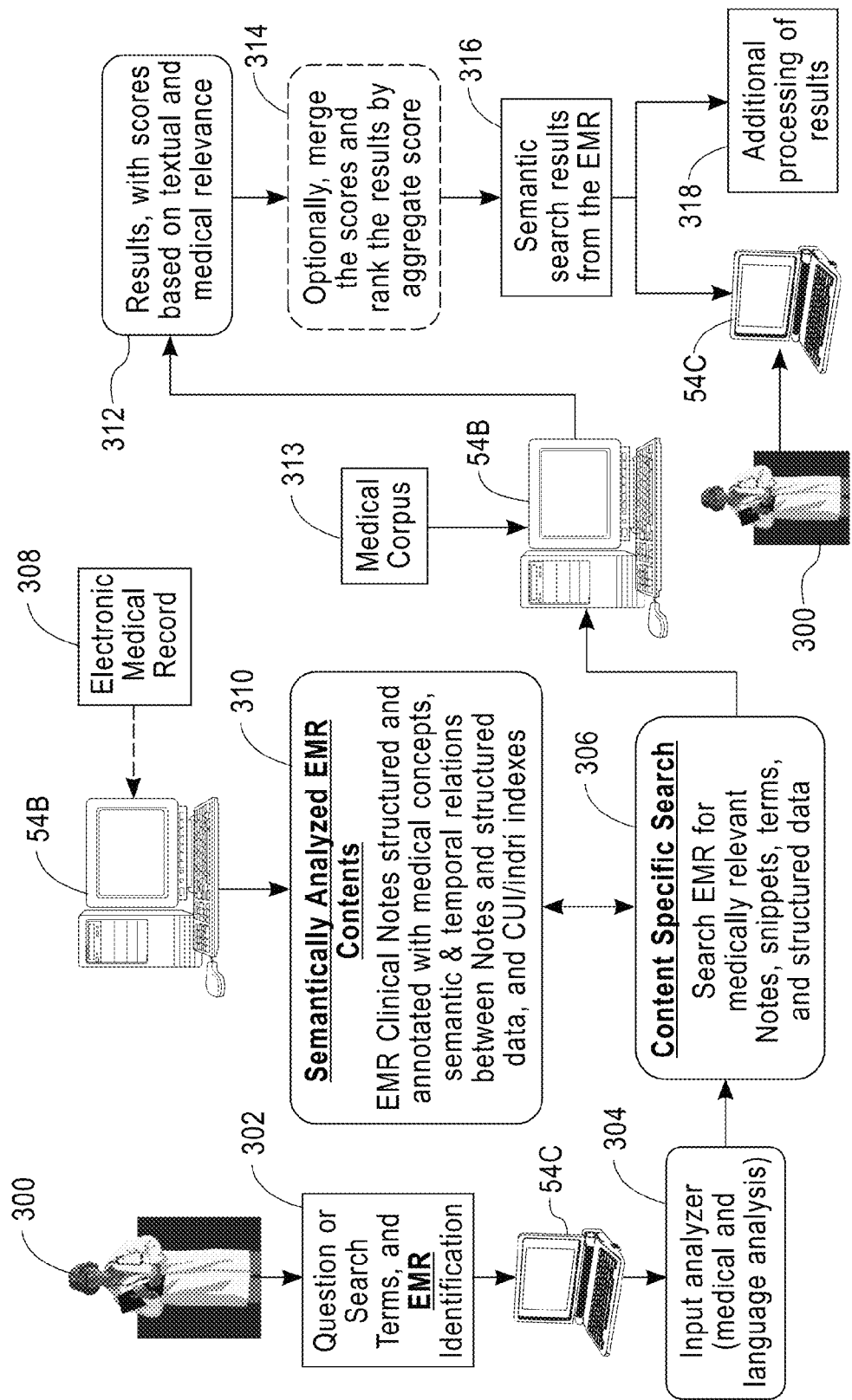
FIG. 1 is a schematic diagram illustrating an exemplary system herein.

It will be readily understood that the systems and methods of the present disclosure, as generally described and illustrated in the drawings herein, may be arranged and designed in a wide variety of different configurations in addition to the systems and methods described herein. Thus, the following detailed description of the systems and methods, as represented in the drawings, is not intended to limit the scope defined by the appended claims, but is merely representative of selected systems and methods. The following description is intended only by way of example, and simply illustrates certain concepts of the systems and methods, as disclosed and claimed herein.

Retrieving relevant content from an Electronic Medical Record (EMR) can be difficult. EMRs may contain large amounts of structured and unstructured data thereby making it difficult to browse the contents for the relevant information. Furthermore, simple keyword searches may find string matches but due to the highly varied medical semantics that exist in the medical domain the results may be under inclusive of the relevant information. Semantic information retrieval languages are available, however, such tools require formulating effective queries and aren't likely to be performed by a medical professional seeking to quickly obtain relevant information from an EMR.

The prevent invention enables medical professionals to quickly retrieve semantically relevant information by submitting queries without requiring any special format and returns both unstructured and structure information from the EMR based on relationships between data within the EMR.

Referring now to the drawings, and more particularly to the system shown in FIG. 1, the system includes one or more computerized devices 54B, 54C (the details of which are discussed in greater detail below in the discussion of FIGS. 7 and 8). Such computerized devices can be connected to one another by a wide area or local network. The one or more computerized devices 54B, 54C that make up the system shown in FIG. 1 may store the EMRs 308 and medical corpora (e.g., books, websites, etc.) 320, as well as process queries, score results, and output results for additional processing or viewing by a user, for example, a medical practitioner.

As used herein, the term "query" is intended to represent any form of search request including both search terms and natural language questions. The queries may be input automatically or manually through any form of computerized device. The term "query" is not intended to be limited in any way other than a request for information from an EMR.

In order to enable a deep semantic search of an EMR, the contents of the EMR, indicated generally as 308, are analyzed semantically and syntactically to recognize features of the EMR 308. The entire contents of the EMR are analyzed including both unstructured documents (e.g. clinician notes) and structured data (e.g. lab results and medications). The semantically analyzed EMR contents 310 are generated to enable a content specific search 306 of the EMR 308.

In FIG. 1, a user 300, such as a medical professional, will select an EMR 308 to search and submit a query 302, such as a natural language question or search term(s), for the relevant information sought from the EMR 308. The query 302 can be provided by a user 300 through one or more computerized devices 54C. The query 302 is analyzed using an input analyzer 304 (that can be operating on one or more computerized devices 54B, 54C, etc.). The input analyzer 304 recognizes semantic features and syntactic features of the query 302. The contents of the query 302 are annotated to identify medical semantic concepts within the query 302 based on the semantic features of the query 302 (for example, using the one or more computerized devices 54B, 54C, etc.). The result of this process produces annotated query contents.

A content specific search 306 is performed against the semantically analyzed EMR contents 310 for medically relevant information in both unstructured and structured data of the EMR (using the one or more computerized devices 54B, 54C, etc.). The results from the unstructured data may include documents/notes, passages, and terms, whereas the results from the structured data may include lists of medications, procedures, or lab results. The results may be returned as relevant to the query based on medical concept relationships identified among entries within the EMR 308 (for example, using the one or more computerized devices 54B, 54C, etc.). The relationships among the medical concepts in the EMR 308 are identified through relationships such as "caused by", "treats", and others. In other words, the relationships may identify the causation of medical conditions and the treatments for medical conditions based on the medical concepts identified in the data. The relationship information may be stored as a data structure on a computerized device.

Query results 312 are obtained from the EMR 308 based on the annotated query contents (using the one or more computerized devices 54B, 54C, etc.). The results can, for example, comprise both passages from the EMR 308 that semantically match the query 302 and passages having a relationship based on the medical concepts identified in the query and the passages. Part of identifying the relationships may include identifying causation of medical conditions and treatments for medical conditions (e.g., "treats", "causes", etc.) based on the medical concepts.

The retrieved results 312 are scored on a variety of measures of semantic match, medical relationship strength, and other criteria (using the one or more computerized devices 54B, 54C, etc.). Results 312 may comprise scores generated in the process of the content specific search 306, or in post-processing utilizing a medical corpus 313. A first score may be determined for the results 312 based on the degree of textual match of the passages in the EMR 308 to the query 302. A second score may be determined for the results 312 based on the strength of medical relationship of the passages or other results in the EMR 308 to the query 302. Similar additional scores for the results 312 may be generated. For example, part of the score may be based on a temporal measure of the relevance of the passages from the EMR 308. That is, more recent entries (i.e., "closer" in time to the time implied in the search) may be more important than other, older entries; therefore, acquiring a higher score. In another example, the method may identify repetitive data in the structured and/or unstructured entries (e.g., the same passage provided in different notes). Part of the score may discount passages having multiple entries (i.e., scoring such repetitive passages lower). As another example, the location of the information within the EMR may be used to generate different scores, for example, data from physician clinical notes may be weighted more heavily that data from administrative notes.

Moreover, the scores can be based on the strength of relationships between the medical problem terms and prescribed medications identified within the EMR, between the medical problem terms and laboratory test results within the EMR, etc.

Optionally, an aggregate score 314 may be produced for the results 312 by automatically merging the various scores. Such merging may, for example, use a weighted average of the scores based on a statistical model. The weighting process can be performed using machine-learning processes to dynamically change weighting to determine how likely the results match the syntax and/or semantics of the query. According to another example, the scores of the results may be combined using machine-learning to generate aggregates scores for each of the results for the patient associated with the EMR. That is, the various scores can be combined; each weighted by a weight determined using a machine-learning technique, into a single weighted score for each answer. Such machine-learning processes can utilize linear regression and classification.

The results having an aggregate score or raw score above a predetermined threshold or thresholds are provided as output 316, in response to the query 302. According to systems and methods herein, the output 316 may be provided to a user 300, such as a medical professional, or to an additional passage analysis engine for additional processing of results, (using the one or more computerized devices 54B, 54C, etc.) as shown at 318.

In other words, a search query 302 is used to retrieve information from an EMR 308. The search query 302 contains search terms for the relevant information sought from the EMR 308. In response to the search query 302, semantically relevant information related to the search terms is provided including clinical notes, medications, test results, treatments, and any other type of information that can be obtained from the EMR. The results of the search include information from the EMR related by medical relationships such as "caused by" or "treats".

Figure 2:
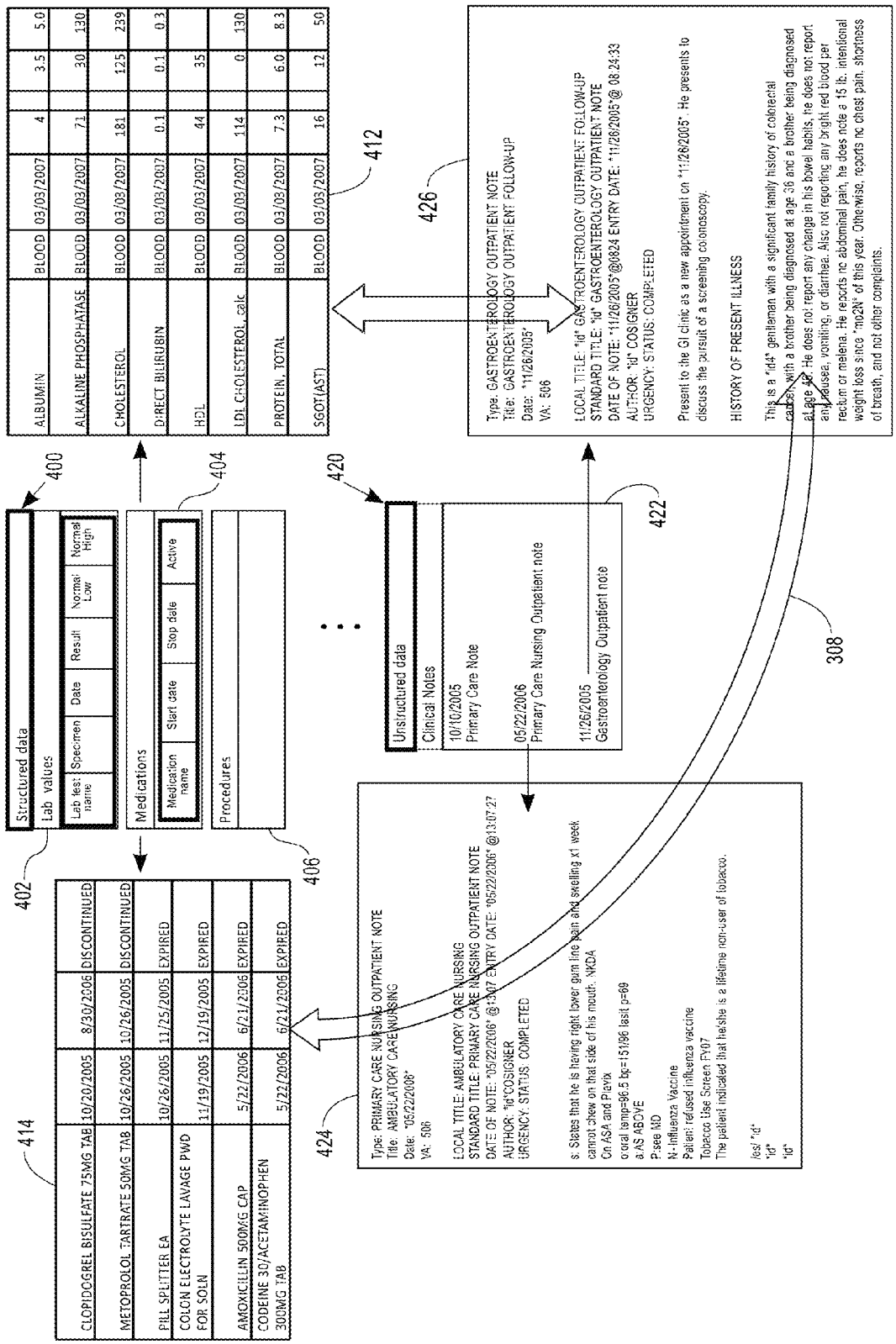
FIG. 2 is a block diagram illustrating relations among components of an EMR according to systems and methods herein.

FIG. 2 is a block diagram illustrating relations among components of an EMR according to systems and methods herein. The EMR 308 may include structured data and unstructured data such as shown in FIG. 2. Structured data 400 may include lab values 402 from specific tests and associated lab value information 412. Information in the lab values 402 may include the specific lab test name, type of specimen, date of the test, test results, and comparative normal low and normal high values. Structured data 400 may include medications 404 for the patient and medication information 414. Information in the medications 404 may include the name of the medication, the start and stop date, and whether the medication is active. Additionally, structured data 400 may include procedures 406, such as medical procedures and tests, for the specific patient. Information in the procedures 406 may include the type of procedure and scheduled date. The EMR 308 may also include unstructured data 420. The unstructured data 420 may include clinical notes 422 containing the details of a particular medical encounter with a medical professional, such as 424 and 426. As depicted by the arrows connecting the clinical note 426 to both medication information 414 and lab value information 412, relationships between unstructured and structured components of the EMR can be identified and stored in the semantically analyzed EMR contents 310. These relationships can then be used to return semantically relevant information to a query from a user. The details regarding how those relationships are identified are explained further with reference to FIG. 3.

Figure 3:
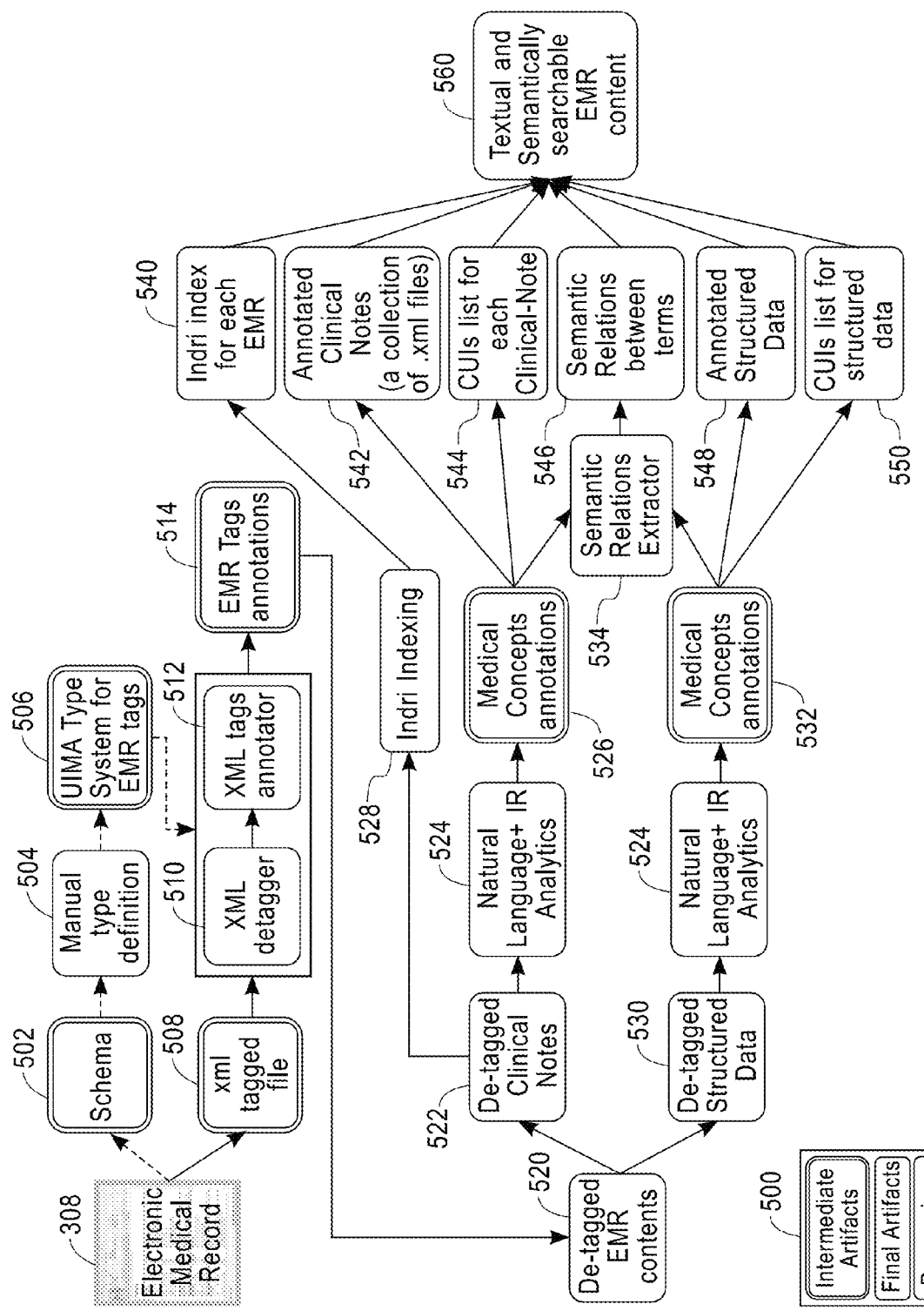
FIG. 3 is a schematic block diagram illustrating various aspects of systems and methods herein.

FIG. 3 illustrates some of the processing steps for extracting semantic relations from the EMR 308 according to systems and methods herein. More specifically, in FIG. 3, the key 500 in the lower left-hand corner indicates that double lined boxes represent intermediate artifacts, boxes with a dotted background indicate final artifacts and single lined boxes represent processing according to systems and methods herein.

For each EMR, a domain expert will manually identify an EMR schema 502 and provide manual type definitions 504. In other words, a domain expert will identify the various sections that exist within the EMR including clinical notes, medications, lab values, procedures, as well as medical concepts within each section and tag each section and medical concept appropriately. An Unstructured Information Management Architecture (UIMA) type system 506 may be applied for the EMR tags provide by the domain expert. UIMA is a software architecture for the development, discovery, and deployment of multi-modal analytics for the analysis of unstructured information and its integration with search technologies. UIMA may be used in medical contexts to analyze clinical notes, such as the Clinical Text Analysis and Knowledge Extraction System (CTAKES). The UIMA process may also add 'tags' to entries in the EMR 308 for identifying various matched concepts and to map the entries to standardized resources. In many cases the clinical notes in an EMR are represented by XML tagged files. For any an XML tag files 508 in the EMR, the XML tags are removed and stored separately as annotations along with the manual annotations as EMR tag annotations 514. The tags are removed in item 512 and, in order to avoid losing the information provided by the previous tags, tag annotations are created in item 514. For example, one such tag annotation can be referred to as "section information". The "section information" tag annotation describes that the tagged item is a section of the EMR. The tag annotations can also contain additional attributes, such as a date, etc. This leaves the de-tagged contents 520 of the EMR ready for processing using natural language and information retrieval analytics.

FIG. 4 is an example of an annotated EMR according to systems and methods herein. Again, in FIG. 4, item 422 represents a clinical note. Item 428 represents annotations pertaining to the clinical note. The annotations part of the interface allows for review of the details of specific note annotations. In addition, item 430 is an example legend showing how the annotations may be categorized. The legend can be used to manage and identify annotations within the clinical note. The purpose of FIG. 4 is to show an example of an annotated EMR as would be produced through the steps 502-514 as shown in FIG. 3. The annotations are typically not seen by the user of the EMR deep semantic search tool.

Returning to FIG. 3, processing of the unstructured data (de-tagged clinical notes 522) and structured data (de-tagged structured data 530) proceeds along parallel paths. More specifically, the de-tagged clinical notes 522 and de-tagged structured data 530 are processed through natural language processing (NLP) and information retrieval (IR) analytics to generate intermediate artifacts of medical concepts annotations 526 and 532. The NLP and IR analytics used may be any techniques known in the art capable of identifying linguistic features from text. The linguistic features may be matched against medical domain taxonomies or ontologies to identify the medical concepts.

Further, as shown by item 528, the de-tagged clinical notes 522 can be subjected to Indri indexing to produce an Indri index for each EMR (item 540). For example, string matching may include Indri search, which is a query built with the input question or search terms and run against the index or a structured data search-a string match within structured data fields. For example, Structured Term Recognition (STR) may recognize new terms of a specific type based on the structure of known terms for that type, e.g. "skin cancer" is a term and is a type of cancer.

As additionally shown in FIG. 3, the medical concepts annotations 526 relating to the de-tagged clinical notes 522 are used to produce annotated clinical notes 542, which are a collection of XML files. The medical concepts annotations 526 relating to the de-tagged clinical notes 522 are similarly used to produce a list of standardized identifiers (CUIs) for each clinical note 544.

In a similar way, the medical concepts annotations 532 relating to the de-tagged structured data 530 are used to produce annotated structured data 548. The medical concepts annotations 532 relating to the de-tagged structured data 530 are similarly used to produce a list of standardized identifiers (CUIs) for the structured data 550. The various final artifacts 540-550 are then combined to produce textural and semantically searchable EMR content as shown by item 560 (shown in FIG. 1 as 310).

The semantic relations extractor 534 utilizes the medical concepts annotations 526 relating to the de-tagged clinical notes 522 and the medical concepts annotations 532 relating to the de-tagged structured data 530 to create semantic relations 546 between the unstructured data and the structured data within the EMR. The semantic relationships generated in item 546 are shown, for example, in FIG. 2, discussed above where the block arrows represent relationships between items of structured data (e.g., test results, lab values, medications) and unstructured data (e.g., clinical notes). For example, in FIG. 2, a curved block arrow illustrates a relationship that has been established by the semantic relations extractor 534 between medication information 414 and the clinical note 426. In this way, the semantic relations extractor 534 has established an otherwise unknown relationship between the structured data 400 and the unstructured data 420. Also, in FIG. 2, a straight block arrow illustrates a relationship that has been established by the semantic relations extractor 534 between lab value information 412 and a clinical note 426. In this way also, the semantic relations extractor 534 has established an otherwise unknown relationship between the structured data 400 and the unstructured data 420.

By establishing otherwise unknown relationships between structured and unstructured data, the semantic relations extractor 534 allows search results that would only produce structured data to also produce unstructured data to which a relationship has been determined by the semantic relations extractor 534. Similarly, the semantic relations extractor 534 allows search results that would only produce unstructured data to also produce structured data to which a relationship has been determined.

In other words, the methods described herein analyze an EMR comprising structured data and unstructured data. In the analysis, a first set of medical concepts 526 is identified from the unstructured data in the EMR and a second set of medical concepts 532 is identified from the structured data in the EMR. Relationships between the medical concepts in the first set of medical concepts and the second set of medical concepts are identified in a medical ontology (explained in more detail below). The relationship information can be stored as a collection for subsequent searching. Optionally, an index of the relationships may be created and stored in a computerized device.

Accurate named entity detectors exist for the medical domain such as the Unified Medical Language System (UMLS). UMLS is a compendium of many controlled vocabularies in the biomedical sciences. The UMLS provides known concept unique identifiers (CUIs) relating to medical disorders. UMLS may be used for identifying medical concept 526, 532, and for extracting relations 534. Relations may also be extracted using other known techniques such as Latent Semantic Analysis (LSA). The semantic relations extractor 534 provides a mapping structure among these vocabularies and thus allows one to translate among the various terminology systems; it may also be viewed as a comprehensive thesaurus and ontology of biomedical concepts. Although the precise terminology of medical language aids in disambiguation, there are special challenges in segmentation and disambiguation. This is evident for acronyms but also for terms like "hypertension" which could be interpreted as "Hypertensive disease" but also as a finding, "Hypertensive adverse event," in the UMLS taxonomy. Furthermore, proper segmentation is used to identify the appropriate level of specificity (e.g., "carcinoma," "pancreatic carcinoma," or "non-respectable pancreatic carcinoma").

In order to use lab findings and other numeric measurements in the medical domain, the semantic relations extractor 534 employs recognition capabilities incorporating context, for instance to identify that "22 y.o." maps to the concept, "Young Adult," or that "320 mg/dL blood glucose" maps to "Hyperglycemia." While in some cases this information may be associated with health records in structured (coded) form that is not always the case. Furthermore, the unstructured medical knowledge sources from textbooks used to generate and score answers are not structured and represent this information only in text or tabular form. In one example, the semantic relations extractor 534 has a rule-based annotator that identifies measurements and test results as expressed in text. Based on existing guidelines, measurements are interpreted to be normal, high, or low, and mapped by the semantic relations extractor 534 using general tables to the corresponding UMLS concept.

Normal, high, and low values may also be expressed lexically (e.g. "elevated T4") and the semantic relations extractor 534 may have trained statistical classifiers and built rule based detectors to identify cases of this. Additionally, the semantic relations extractor 534 has collected a set of mapping rules to map to specific concepts in UMLS when they exist (e.g., mapping from "blood pressure is elevated" to the "Hypertension" concept). Negation may be considered a unary relation and we have adapted and enhanced NegEx to work with the system parser to identify concepts that are negated.

Once the textually and semantically searchable EMR content 560 is generated, the content may be searched by a user by inputting a query for content retrieval. Multiple semantic search techniques may be employed against the searchable EMR content 560, such as string matching, Latent Semantic Analysis (LSA) search, Logical Form Answer Candidate Scorer (LFACS) term matching, and relations-based search.

String matching may be run against an Indri index or by matching against terms in the structured data fields. String matching is a common information retrieval technique and useful in making sure the results contain any information with matching terms from the query.

Latent Semantic Analysis is an unsupervised technique, which the methods herein use to produce a latent semantic index over the medical corpus. This index loosely captures "topics" as they occur in the corpus. Then, at results scoring time, a LSA similarity is computed between the terms in the query and the terms associated with the result in the LSA index. LSA searching may incorporate pair-wise matching of each CUI from each note in the EMR with all CUIs in the input. For example, LSA recognizes statistical association between two entities such as words, CUIs, or terms, based on their occurrence in the corpus. For example, Hyperlipidemia and High Cholesterol are likely to be similar based on co-occurrence. Both unstructured and structured data may be returned as semantically relevant results using LSA. LSA can be used to determine the strength of the relationship between a CUI and a medical prescription or a lab test result. A CUI path may show relationships between disorders, and the paths may show relationships between treatments (medicine, procedures) and lab results. These confidence measures, frequencies, strengths, relationships, etc., are included to generate scores for each of the features.

In LFACS term matching, each term from each data item, for example a clinical note, medication, lab result, is semantically matched with terms from the query. Those results having a number of matches over a predetermined threshold may be kept.

A relations-based search uses relations between the structured data and unstructured data to extract relevant portions of clinical notes. For example, given an identified medication from the EMR, and a semantic relationship identifying a "treats" relation between that medication and a disease, then the relation may be used to identify and extract a relevant portion of a clinical note identifying that particular disease.

Once all potentially relevant results are obtained using the various searching techniques described above, then the retrieved results may be scored on a variety of measures of semantic match, medical relationship strength, and other criteria. At least one first score may be determined for the results based on the degree of semantic match of the results to the query. A second score may also be determined for the results based on the strength of medical relationship of the results to the query. Other appropriate scores for the results may be determined.

If the query is expressed as a natural language question, then a type-matching score may be employed. Typing information is available in domain taxonomies as well as extractions from domain text content. Entity disambiguation is used to map results from text into the medical taxonomies. Lexical answer types (LATs) expressed in the query may also be mapped through predicate disambiguation to types in the taxonomy. Once both the result and LAT have been mapped to concepts in the taxonomy, specialized techniques can produce scores based on ancestry and other metrics over the hyponymy tree to identify if the result is of the right type.

The following are some additional examples of scorers and features. A symptom scorer generates a feature based on the specific patient's presented data. A time-based scorer may reason about the trend of information over a period of time or a temporal measure of the relevance of the passages. A severity scorer may use information about the features to predict mortality, etc. Other scorers assign relative values from the text description of the features.

The scorers herein may range from simple heuristics rules using shallow lexical pattern matching to deeper semantic reasoning scorers supported by evidence sources and domain ontologies. As an example of a simple heuristic, the presence of certain keywords, or their combinations, in the feature description could be used by a scorer to assign a feature value. Similarly, a temporal scorer could use temporal concepts (e.g., DateTime, durations) and relations to estimate the time overlap. Additionally, heuristic-based scorers herein can directly evaluate the impact of the features on the recommended analytics. Past instances of treatment actions that interacted with known features may be used as off-line training data to develop the learned models. Results of action or inaction can be recorded for training of future diagnoses.

Figure 5A:
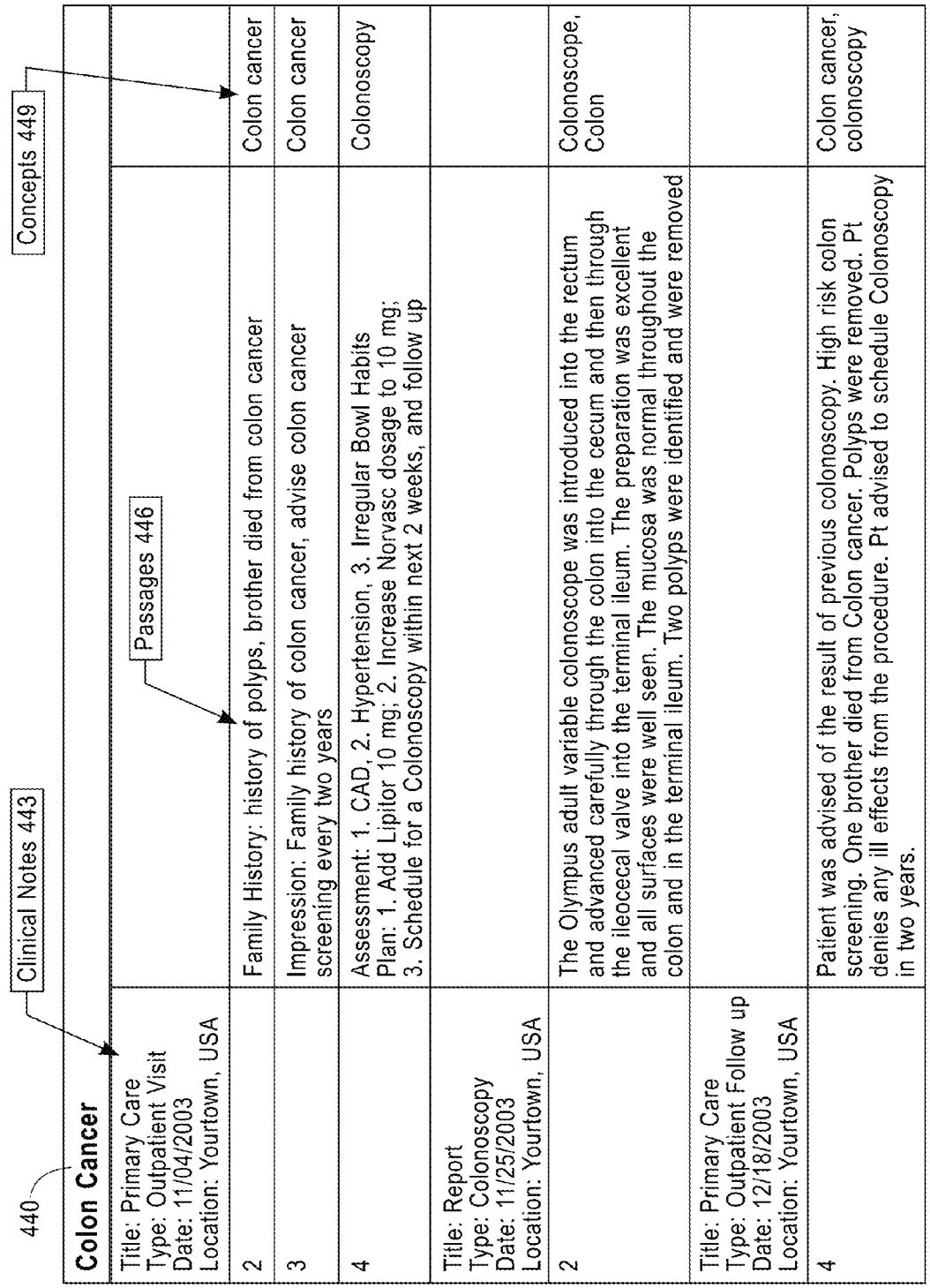

FIG. 5A illustrates exemplary results according to the present invention for the query of "colon cancer" 440. For example, the results can include clinical notes 443, passages from clinical notes 446, and concepts from passages 449. In the example shown in FIG. 5A, a search for colon cancer 440 may result in clinical notes 443 concerning a meeting between the patient and a primary care provider. The displayed results may be ordered or coded, such as with different colors, to indicate a score representing the relevance of the results to the query.

FIG. 5B illustrates exemplary results for the query "ht" 452. The results may be categorized based on the type of match, for example, a semantic match tab 455, a contradicted tab 461, a more general tab 464, a lab tests tab 467, a medications taken tab 468 and a medications ordered tab 469. The search results may be obtained from the structured or unstructured data. As shown on left side of the interface, the results obtained for the query include thirteen clinical notes containing passages related to hypertension. In this example, the query is a common shorthand version of the medical term 'hypertension' 488 and by employing aspects of the present invention the results returned include information from the EMR semantically related to hypertension even though the shorthand version was used. This demonstrates how aspects of the present invention described here allow a user, such as a medical practitioner, to obtain relevant information from an EMR without having to be concerned query structure or semantics.

FIG. 5C illustrates exemplary search results for a query containing multiple search terms related to the Thyroid 470. The results shown include a list of ordered medications from a structured data portion of the EMR. As shown on the left side of the interface, the results obtained for the query include five orders for medications that treat medical problems related to the Thyroid. As shown at 473, a selection of the first ordered medication in the list of results then highlights the details of the ordered medication on the right side of the interface.

Figure 6:
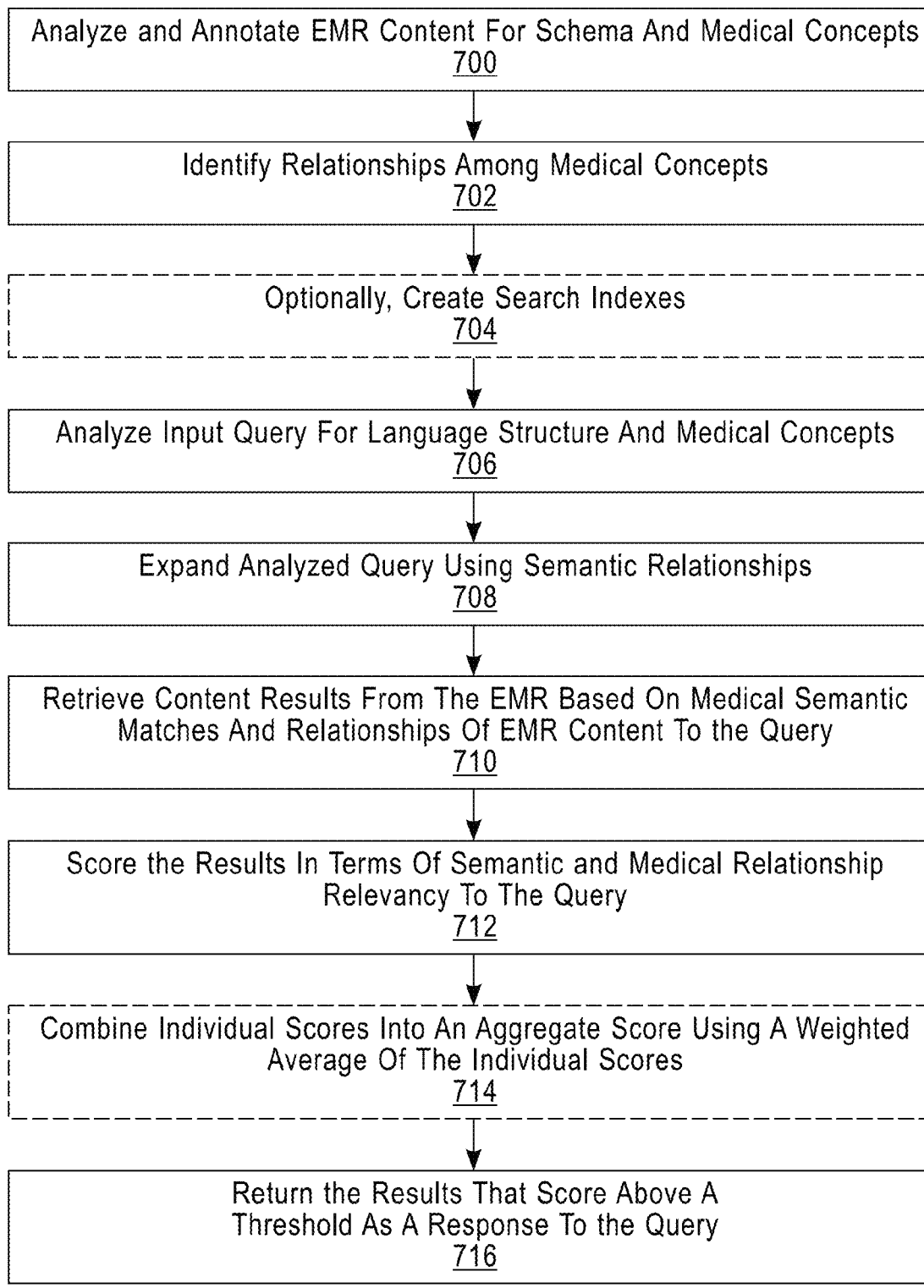
FIG. 6 is a flow diagram illustrating systems and methods herein.

FIG. 6 is a flow diagram illustrating the processing flow of an exemplary method of analyzing an EMR. In item 700, the EMR contents are extracted and organized to recognize the structure of the EMR and to facilitate subsequent processing of the EMR contents. The contents of each EMR are analyzed and annotated to identify the EMR schema and medical semantic concepts in them. At 702, relationships are identified among the medical concepts in the EMR contents. In some cases, search (inverted) indexes may be created on the EMR content, at 704. The search indexes enable retrieval of passages that match a given input syntactically and semantically. At 706, in response to a query on the EMR, the query is analyzed and annotated to identify the syntactic structure and medical semantic concepts. At 708, the analyzed query is expanded using semantic relationships such as "treats" and "caused by". At 710, the analyzed and expanded input query is used to search the EMR contents. The query retrieves matching content results from the EMR, including clinical notes, passages, terms and structured information, based on medical semantic matches and the relationships of the EMR content to the input query. At 712, the results are scored (producing a set of scores) based on their semantic match to the input query, the medical relationship strength to the input query, and other criteria. Optionally, the individual scores may be combined into an aggregate score, at 714. The aggregate score may use a weighted average of the individual scores, which may be obtained using a statistical training process. At 716, the results that have an aggregate score above a predetermined threshold are returned in response to the input query.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

In the on-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 9:
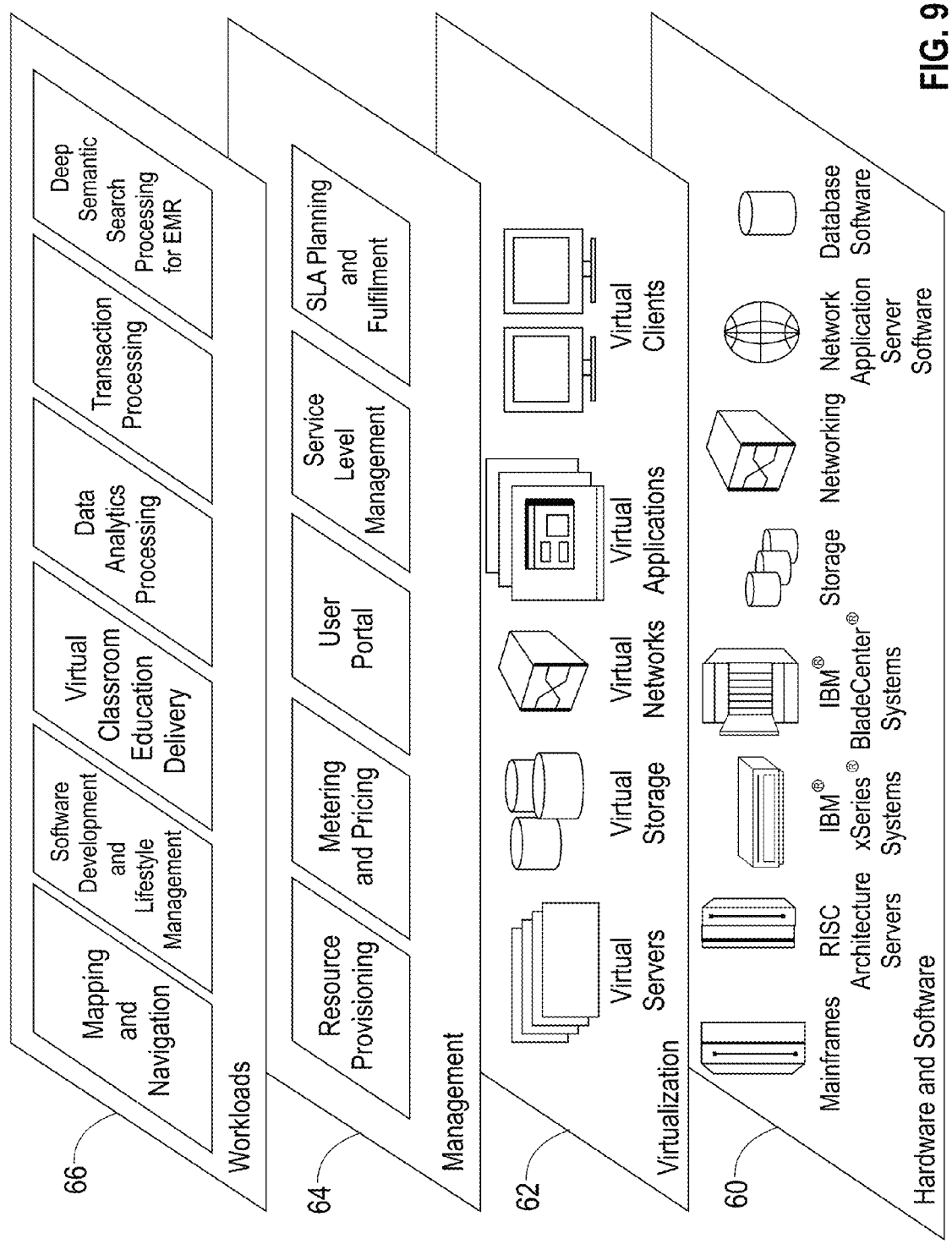
FIG. 9 is a schematic diagram of functional abstract layers according to systems and methods herein.

Referring now to FIG. 9, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

Figure 7:
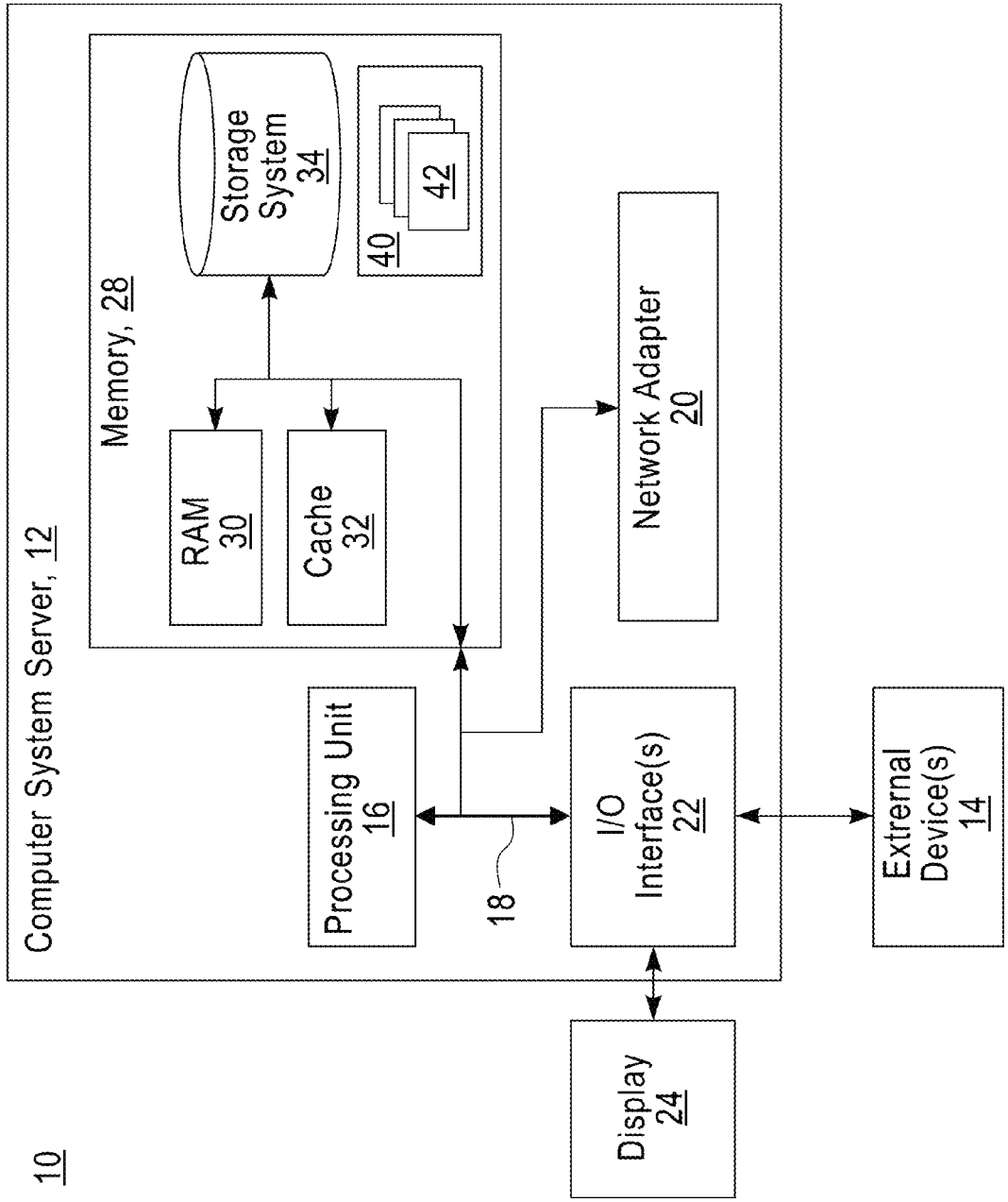
FIG. 7 is a schematic diagram of a hardware system according to systems and methods herein.

As shown in FIG. 7, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 8:
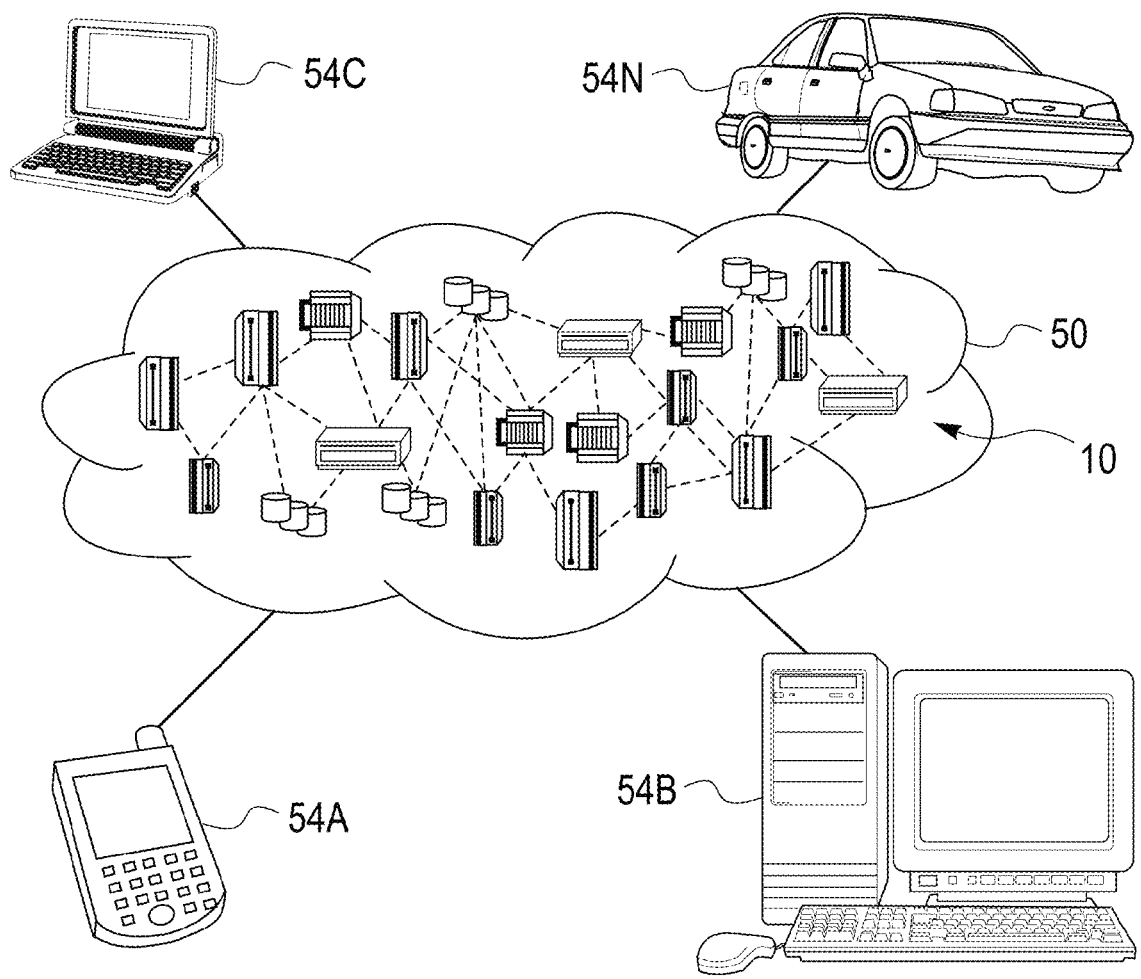
FIG. 8 is a schematic diagram of a computing environment according to systems and methods herein.

Referring now to FIG. 8, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Referring now to FIG. 9, a set of functional abstraction layers provided by cloud computing environment 50 (FIG. 8) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and deep semantic search processing of an EMR according to the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    receiving a query for information from an electronic medical record (EMR) comprising structured data and unstructured data;
    annotating contents of said unstructured data and said structured data to produce annotations;
    using said annotations to create concept unique identifiers (CUIs);
    identifying clinically relevant semantic relationships between said structured data and unstructured data in said EMR based on statistical associations between said CUIs;
    producing a score for relevant information from said EMR that is semantically related to said query based on strength of said clinically relevant semantic relationships between said structured data and unstructured data; and
    prioritizing a display of said relevant information based on said score; and
    providing, in response to said query, said relevant information, said relevant information comprising at least one of clinical notes, medications, test results, treatments, and contraindications.

2. The method according to claim 1, further comprising: determining whether EMR data is semantically relevant to said query based on medical relationship relevancy.

3. The method according to claim 1, further comprising:
    identifying a first set of medical concepts from said unstructured data in said EMR;
    identifying a second set of medical concepts from said structured data in said EMR; and
    identifying clinically relevant semantic relationships in a medical ontology between medical concepts in said first set of medical concepts and said second set of medical concepts.

4. The method according to claim 3, further comprising:
    creating inverted search indexes on said first set of medical concepts and said second set of medical concepts, said inverted search indexes enabling retrieval of passages matching said query syntactically and semantically.

5. The method according to claim 3, said identifying clinically relevant semantic relationships in said medical ontology between medical concepts in said first set of medical concepts and said second set of medical concepts further comprising:
   identifying causation of medical conditions and treatments for medical conditions based on said medical concepts.

6. The method according to claim 1, further comprising:
   outputting results of said query in textual form to a user interface.

7. The method according to claim 1, said CUIs comprise standardized identifiers relating to medical disorders related to said information in said unstructured data and said structured data.

8. A method comprising:
   analyzing an electronic medical record (EMR) comprising structured data and unstructured data;
   annotating contents of said unstructured data and said structured data to produce annotations;
   using said annotations to create concept unique identifiers (CUIs), said analyzing comprising:
      automatically identifying a first set of medical concepts from said unstructured data in said EMR;
      automatically identifying a second set of medical concepts from said structured data in said EMR; and
      automatically identifying clinically relevant semantic relationships in a medical ontology between medical concepts in said first set of medical concepts and said second set of medical concepts in said EMR based on statistical associations between said CUIs;
   producing a score for relevant information from said EMR that is semantically related to a query based on strength of said clinically relevant semantic relationships between said first set of medical concepts and said second set of medical concepts;
   prioritizing a display of said relevant information based on said score;
   storing relationship information as a data structure in a computerized device; and
   providing, in response to said query, said relevant information.

9. The method according to claim 8, said automatically identifying relationships in a medical ontology between medical concepts in said first set of medical concepts and said second set of medical concepts further comprising:
   identifying causation of medical conditions and treatments for medical conditions based on said medical concepts.

10. The method according to claim 8, further comprising:
    receiving a query containing search terms for information from said EMR; and
    retrieving semantically relevant results from said EMR related to said search terms in response to said query using a search index.

11. The method according to claim 10, further comprising:
    outputting retrieved semantically relevant results.

12. The method according to claim 8, said CUIs comprise standardized identifiers relating to medical disorders related to said information in said unstructured data and said structured data.

13. A system comprising:
    a storage system storing electronic medical records (EMRs) comprising structured data and unstructured data;
    an I/O interface configured to receive a query for information from an EMR; and
    a processing unit,
    said processing unit being configured to annotate contents of said unstructured data and said structured data to produce annotations,
    said processing unit being configured to use said annotations to create concept unique identifiers (CUIs),
    said processing unit being configured to identify clinically relevant semantic relationships between said structured data and unstructured data in said EMR based on statistical associations between said CUIs,
    said processing unit being configured to produce a score for relevant information from said EMR that is semantically related to said query based on strength of said clinically relevant semantic relationships between said structured data and unstructured data,
    said processing unit being configured to prioritize a display of said relevant information based on said score, and
    said I/O interface begin configured to generate results to said query based on said relevant information, wherein said results comprise at least one of clinical notes, medications, test results, treatments, and contraindications.

14. The system according to claim 13, said CUIs comprise standardized identifiers relating to medical disorders related to said information in said unstructured data and said structured data.

15. A computer program product for creating a semantically searchable electronic medical record, said computer program product comprising a computer readable storage medium having program instructions embodied therewith, the program instructions being readable/executable by a processor, to cause said processor to perform a method comprising:
    receiving a query for information from an electronic medical record (EMR) comprising structured data and unstructured data;
    annotating contents of said unstructured data and said structured data to produce annotations;
    using said annotations to create concept unique identifiers (CUIs);
    identifying clinically relevant semantic relationships between said structured data and unstructured data in said EMR based on statistical associations between said CUIs;
    producing a score for relevant information from said EMR that is semantically related to said query based on strength of said clinically relevant semantic relationships between said structured data and unstructured data;
    prioritizing a display of said relevant information based on said score; and
    providing, in response to said query, said relevant information,
    said relevant information comprising at least one of clinical notes, medications, test results, treatments, and contraindications.

16. The computer program product according to claim 15, said method further comprising:
    determining whether EMR data is semantically relevant to said query based on medical relationship relevancy.

17. The computer program product according to claim 15, said method further comprising:

identifying a first set of medical concepts from said unstructured data in said EMR;

identifying a second set of medical concepts from said structured data in said EMR; and identifying clinically relevant semantic relationships in a medical ontology between medical concepts in said first set of medical concepts and said second set of medical concepts.

18. The computer program product according to claim 17, said identifying clinically relevant semantic relationships in said medical ontology between medical concepts in said first set of medical concepts and second set of medical concepts further comprising:

identifying causation of medical conditions and treatments for medical conditions based on said medical concepts.

19. The computer program product according to claim 15, further comprising:

outputting results of said query in textual form to a user interface.

20. The computer program product according to claim 15, said CUIs provide standardized identifiers relating to medical disorders related to said information in said unstructured data and said structured data.

\* \* \* \* \*